(12) United States Patent
Karol et al.

(10) Patent No.: US 7,015,465 B2
(45) Date of Patent: Mar. 21, 2006

(54) PARALLEL CONCENTRATION, DESALTING AND DEPOSITION ONTO MALDI TARGETS

(75) Inventors: Robert Karol, Marlboro, MA (US);
Jeffrey Finch, Mendon, MA (US);
Daniel Wall, Shrewsbury, MA (US)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 10/834,780

(22) Filed: Apr. 29, 2004

(65) Prior Publication Data

US 2004/0262513 A1    Dec. 30, 2004

Related U.S. Application Data

(63) Continuation of application No. PCT/US02/36950, filed on Nov. 18, 2002.

(60) Provisional application No. 60/339,087, filed on Nov. 16, 2001.

(51) Int. Cl.
*H01J 49/00* (2006.01)
*B01D 15/08* (2006.01)

(52) U.S. Cl. ............... 250/288; 250/281; 250/282; 250/287; 250/423 R; 250/424; 250/425; 436/518; 436/519; 427/421.1; 427/422; 210/198.2; 210/656; 210/659

(58) Field of Classification Search ............... 250/288, 250/281, 282, 287, 424, 425, 423 R, 423 P; 210/198.2, 656, 659; 427/421.1, 422, 424; 436/518, 519, 161
See application file for complete search history.

(56) References Cited

U.S. PATENT DOCUMENTS

| | | | |
|---|---|---|---|
| 5,376,277 A * | 12/1994 | Cortes et al. ............... | 210/659 |
| 5,770,272 A | 6/1998 | Biemann et al. | |
| 5,772,964 A | 6/1998 | Prevost et al. | |
| 6,175,112 B1 | 1/2001 | Karger et al. | |
| 6,296,771 B1 * | 10/2001 | Miroslav ................. | 210/656 |
| 6,358,692 B1 | 3/2002 | Jindal et al. | |
| 6,410,914 B1 * | 6/2002 | Park et al. ................ | 250/288 |
| 6,436,292 B1 * | 8/2002 | Petro ....................... | 210/656 |
| 6,491,816 B1 * | 12/2002 | Petro ....................... | 210/198.2 |
| 6,633,031 B1 * | 10/2003 | Schultz et al. ............ | 250/288 |
| 6,653,627 B1 * | 11/2003 | Guevremont et al. ...... | 250/288 |
| 6,776,902 B1 * | 8/2004 | Petro ....................... | 210/198.2 |
| 6,818,134 B1 * | 11/2004 | Lemmon et al. .......... | 210/656 |
| 6,858,435 B1 * | 2/2005 | Chervet et al. ........... | 436/161 |
| 2002/0020670 A1 * | 2/2002 | Petro ....................... | 210/656 |
| 2002/0190001 A1 * | 12/2002 | Petro ....................... | 210/656 |
| 2003/0070988 A1 * | 4/2003 | Petro et al. ............... | 210/656 |
| 2004/0084374 A1 * | 5/2004 | Lemmon et al. .......... | 210/656 |
| 2004/0262513 A1 * | 12/2004 | Karol et al. .............. | 250/288 |

OTHER PUBLICATIONS

K. Wagner, et al, Protein mapping by two-dimensional high performance liquid chromatography, Journal OFChromatography, A, 893 (2000) 293-305.

\* cited by examiner

*Primary Examiner*—John R. Lee
*Assistant Examiner*—Bernard E. Souw
(74) *Attorney, Agent, or Firm*—Brown Rudnick Berlack and Israels LLP

(57) ABSTRACT

A method and apparatus for the continuous deposition of RP HPLC eluent, from isocratic or gradient elutions, on to a MALDI target using a parallel sample desalting method, allows increased sensitivity of the MALDI sample by preconcentration of the analyte, separation of interfering contaminants from the analyte and increased dynamic range of peptide abundance that can be analyzed. The parallel processing of sample material allows greater throughput than that of manual methods.

22 Claims, 6 Drawing Sheets

PARALLEL CONCENTRATION, DESALTING AND DEPOSITION ONTO MALDI TARGETS

CROSS REFERENCE RELATED APPLICATION INFORMATION

This application claims priority from U.S. Provisional Patent Application No. 60/339,087, filed Nov. 16, 2001 and is a continuation of PCT application number PCT/US02/36950, filed Nov. 18, 2002. The contents of these applications are incorporated herein by reference.

STATEMENT ON FEDERALLY SPONSORED RESEARCH

N/A

FIELD OF THE INVENTION

This invention relates to automated preparation of MALDI targets for proteins, peptides, and nucleic acids by use of parallel reversed phase columns.

BACKGROUND OF THE INVENTION

Although genomics has advanced the genetic basis of biological processes, it has significant limitations in understanding the complete biological process. It is therefore now generally accepted that the biological process cannot be completely defined or understood solely by the genetic sequence or MRNA transcripts. A complete understanding of the biological process must entail the structure and dynamics of proteins. The study of the protein complement of the genome is commonly referred to as Proteomics.

The function of products encoded by identified genes and especially by partial cDNA sequences are frequently unknown as is information about post-translational modifications (such as glycosylation and phosphorylation) that can profoundly influence their biochemical properties. Protein expression is often subject to post-translational control, so that the cellular level of an mRNA does not necessarily correlate with the expression level of its gene product. Automated techniques for random sequencing of nucleic acids involve the analysis of large numbers of nucleic acid molecules prior to determining which, if any, show indications of scientific significance. For these reasons, there is a need to supplement genomic data by studying the patterns of protein expression, and of post-translational modification, in a biological or disease process through direct analysis of proteins and protein digests.

Technical constraints, however, have heretofore limited the automated, cost-effective, reproducible, systematic analysis of proteins and other biomolecules present in biological samples. Analyzing biomolecules such as proteins needs to be substantially automated to avoid time consuming, labor intensive, expensive, and inefficient detection, imaging, purification and analysis.

One of the most robust methods of analysis of biological samples is Matrix-Assisted Laser Desorption/Ionization Time-of-Flight Mass Spectrometry (MALDI-TOF/MS). Sample analysis by MALDI is generally known to be a simple technique with high sensitivity without the use of chromatographic separation prior to analysis. MALDI currently allows precise measurements of masses of peptides from protein digests having molecular weights ranging from about 500 to 5000 daltons, as well as intact proteins up to 100,000 Da. While single protein digests can be analyzed by MALDI-TOF/MS to generate peptide mass fingerprints (PMF) that identify the protein when a set of proteins from a sample are mixed together, detection of such a set by PMF provides more challenges for identification by PMF. The protein digests can also be analyzed in MALDI-MS/MS instruments that allow for the fragmentation of individual peptides and subsequent sequencing and identification of the protein from which that peptide originated.

The present detection limits with mass spectrometry, especially MALDI, depend on getting a sample concentrated and onto a small target area. Unfortunately, present methods of concentrating a sample onto a MALDI target include the use of laboratory tools such as pipette tips containing resin attached at their very tip occupying about 0.5 $\mu$l volume, such as ZipTip™ (Millipore, Bedford, Mass.). This method of transfer using ZipTips suffers from a diffential loss of sample material that is adsorbed to the surface of the resin bed and consequently this method is not practical for protein digests where poor recovery is an issue.

Analysis of biological samples by MALDI is currently a process that is primarily an off-line technique that requires manual or automated preparation of a sample mixed with a matrix material. This off-line preparation requires a great deal of expertise and a corresponding significant amount of time. The process can be automated by use of liquid handling robots and ZipTips or by use of a system to desolvate the eluent from some desalting column. For the latter case prior attempts to automate this off-line process have been met with technical constraints.

In U.S. Pat. No. 6,175,112 to Karger et al., a universal interface for continuous on-line liquid sample introduction directly to a time-of-flight mass spectrometer is described. Unfortunately this attempt to automate and therefore increase the throughput and utility of MALDI-TOF mass spectrometry suffers from several deficiencies. The eluent flow rate of Karger is limited to less than about 300 nanoliters per minute and therefore larger scale chromatography, such as capillary liquid chromatography, cannot be accommodated without a post column split. Further, the liquid junction of the fused silica tip is subject to plugging and the silica tip requires frequent replacement. Additionally, the Karger configuration requires a separate auxiliary pump for matrix flow into the liquid junction and vacuum chamber.

SUMMARY OF THE INVENTION

Sample analysis by MALDI is generally known to be a simple technique with high sensitivity and relative intolerance to impurities without the need for chromatographic separations prior to analysis. In contrast other techniques such as electrospray often need to exploit the advantages of chromatographic separation prior to analysis. The inventive system and method exploits the potential advantages for MALDI from the continuous deposition of Reverse Phase High Pressure Liquid Chromatography ("RP HPLC") eluent on to a MALDI target using a parallel column desalting method. This inventive method allows increased sensitivity for the MALDI by pre-concentrating the analyte and separation of interfering contaminants from the analyte. A further advantage that results from the parallel processing of sample material is greater throughput than that of manual methods. The automation of sample deposition allows the chromatographic eluent to be frozen in time on a MALDI target which may be stored for analysis at a later time by other techniques.

The inventive method allows the eluent from a reversed phase HPLC peptide separation to be parallel processed and continuously deposited onto a MALDI sample plate (precoated with αCHCA matrix). The peptides are obtained by digesting protein mixtures with tryspin. The protein mixtures vary in complexity from standard proteins to hundreds of proteins depending on the length of the separation and the use of either MALDI-TOF/MS or MALDI-MS/MS methods.

All digests are then separated by an automated parallel processing by multiple RP HPLC columns. The eluent and pepitdes from the RP HPLC columns are collected and deposited onto MALDI targets while the solvent substantially is removed by heat and use of a coaxial nebulizer gas. These targets are then analyzed using MALDI-TOF MS and MALDI-MS/MS. It is contemplated within the scope of the invention that other methods of detection known in the art may be used.

The peptide mass maps and peptide sequencing information that are generated by the inventive method are used to determine the identity of the proteins therein. The automated inventive method to parallel process and continuously deposit sample produced by RP HPLC peptide separations onto a MALDI target plate allows for greater throughput. Additionally, when a separation is used in the parallel columns, the inventive method offers improved peptide mass mapping coverage over prior art spotting methods in terms of the sequence coverage and the dynamic range of proteins that can be identified from one mixture.

BRIEF DESCRIPTION OF THE DRAWINGS

The foregoing and other features and advantages of the present invention will be more fully understood from the following detailed description of illustrative embodiments, taken in conjunction with the accompanying drawing in which.

DETAILED DESCRIPTION

The instant invention provides an inventive apparatus and methods for the parallel concentration, desalting and deposition of biological samples onto MALDI targets. This deposition of biological samples is accomplished with greater throughput and reliability of existing methods.

Figure 1:
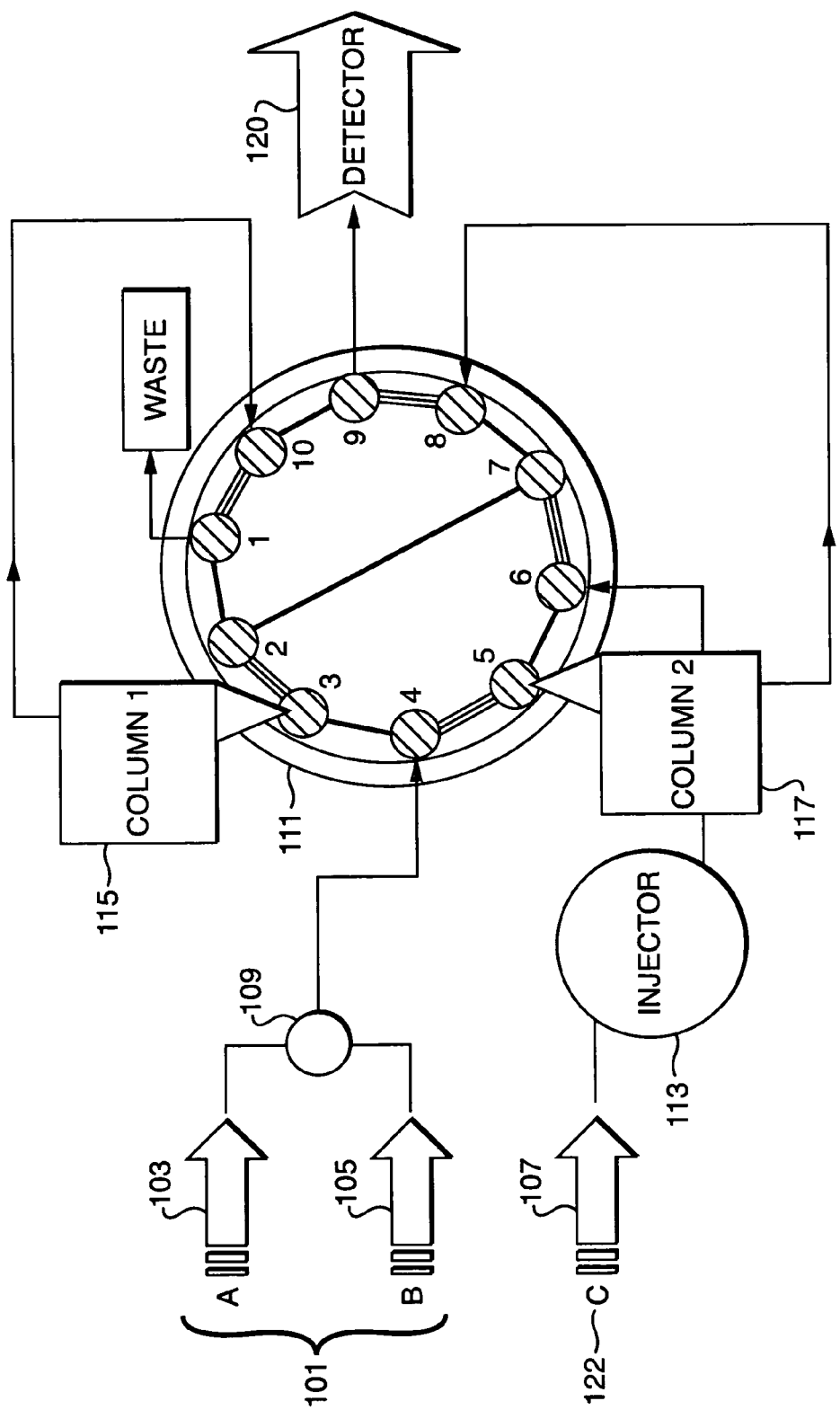
FIG. 1 is a schematic of an inventive 10 port valve configuration with two trapping columns allowing for parallel desalting of digest (shown in a first position)

FIG. 1 illustrates the general schematic of the inventive system and method for the deposition of biological samples onto a MALDI target. Turning to FIG. 1 the system contains a conventional gradient system. The gradient system in this illustrative embodiment comprises a first pump 103, a second pump 105 and a third pump 107. These pumps 103, 105, and 107 are independent reciprocating syringe pumps. In this illustrative embodiment these pumps 103, 105, 107 are configured in the CapLC™ (Waters Corporation, Milford, Mass.) Auxiliary Mode. It is contemplated within the scope of this invention that other pumps known in the art may be used such as used in the Alliance system (Waters Corporation, Milford, Mass.) or the like. The first pump 103 and the second pump 105 comprise a gradient pump system 101. This gradient pump system 101 deliverers solvents into separation or trapping columns within the inventive system. These pumps 103 and 105 are in fluidic communication with a common mixing tee 109.

The gradient pumping system 101 pumps a first solvent through the first pump 103 and a second solvent through the second pump 105. The solvents contemplated within the scope of the invention are those known in the art for chromatographic separations such as water, acetonitrile, methanol, ethanol, propanol, trifluoroacetic acid, formic acid, acetic acid, or the like. The common mixing tee 109 is in fluid communication with a ten port switching valve 111. In this illustrative embodiment the ten port switching valve 111 is a valve commonly available from Valco (Houston, Tex.). It is contemplated within the scope of the invention that other multi-port switching valves may be used such as a Rheodyne valve available from Rynodene, L.P., Rohnert Park, Calif., or the like. It is contemplated within the scope of the invention that other multi-port valves having more or less than 10 ports known in the art may be used or that multiple multi port switching valves may be used.

The multi port switching valve 111 allows the parallel processing of samples. It should be understood by those skilled in the art that increases in parallel processing can be achieved by the use of multi port valves in excess of the instant ten port switching valve 111. The use of multiple port switching valves in tandem having a greater number of ports allows for additional components such as columns, solvent delivery systems, auto-samplers and detectors. The ten port switching valve 111 is in fluid communication with an auxiliary isocratic pump 122. The auxiliary pump 122 uses the third pump 107 to pump sample from an auto sample injector 113 to the ten port switching valve 111. The third pump 107 within the gradient system is a CapLC, (Waters Corporation) single syringe pump. It is contemplated within the scope of the invention that more than one auto sampler with a corresponding additional pump may be used to deliver sample. The auto sampler injector 113 is in fluid communication with the ten port valve 111.

The ten port valve 111 is in fluid communication with a first column 115 and a second column 117. In this illustrative embodiment the columns 115, 117 are Symmetry 300™ C18 5 um OPTI-PAK™ trapping columns, Waters Corporation, Milford, Mass. These trapping columns 115, 117 are reversed phase columns that allow for the concentration and desalting of samples prior to analysis. It is contemplated within the scope of the invention that other reversed phase chromatography columns known in the art may be used such as Xterra or Atlantis columns, Waters Corporation, Milford, Mass., or the like. It is further contemplated that other chromatography columns such as ion exchange or size exclusion may be used to increase the capacity of the multidimensional separation system.

The connection of the first column 115 and second column 117 to the ten port switching valve 111 allows multiple samples to be parallel processed within the inventive system.

Figure 2:
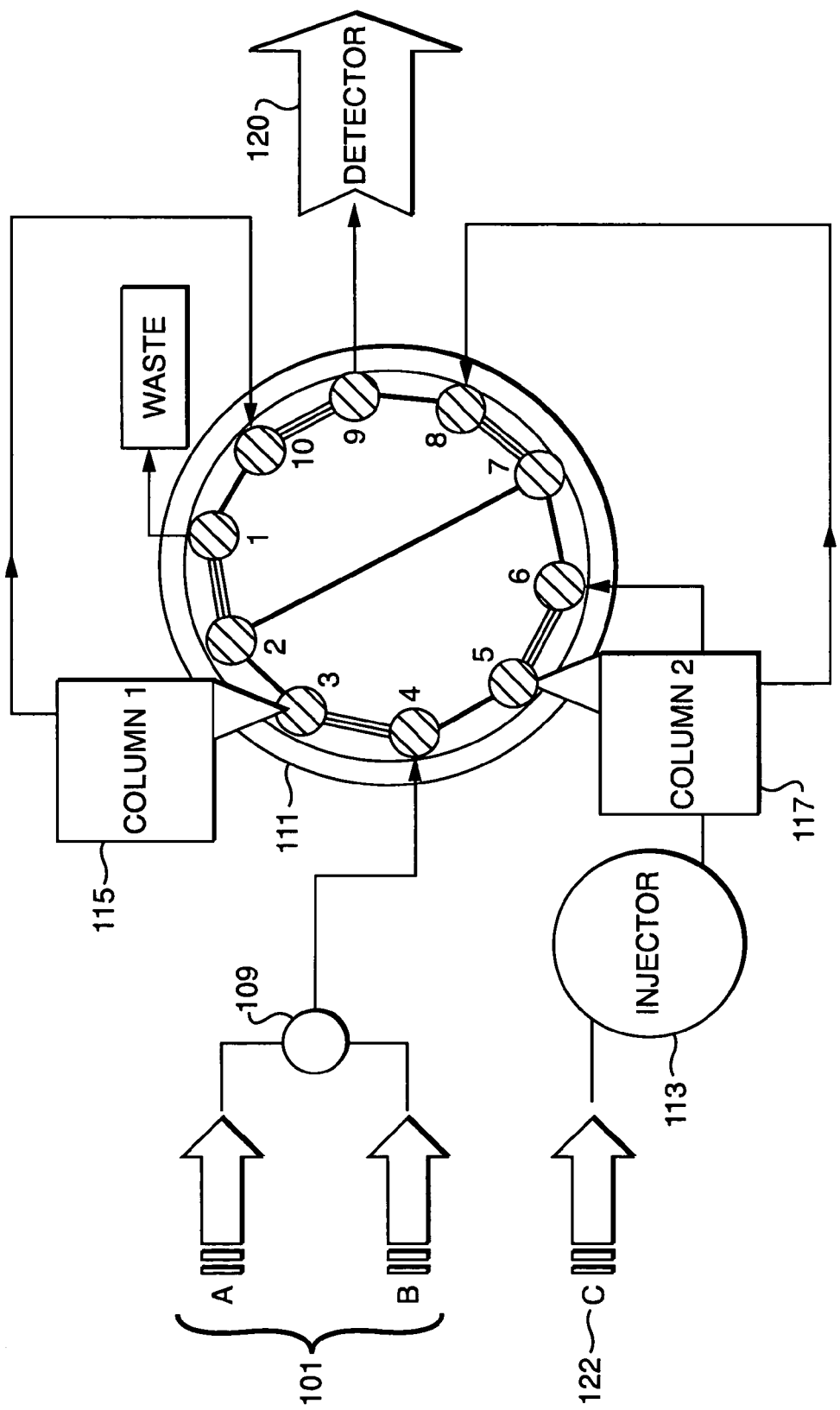
FIG. 2 is a schematic of the inventive 10 port valve configuration with two trapping columns allowing for parallel desalting of digest (shown in a second position)

In the first illustrative embodiment depicted in FIG. 1, the parallel processing of samples is achieved by injecting a second sample from the auto sampler 113 into the second column 117, while a first sample is eluted form the first column and delivered to a deposition module 120 such as LC-MALDIprep™, Waters Corporation, Milford, Mass., while the ten port valve 111 is in a first position. Turning to FIG. 2 this parallel processing of sample is further shown by the ten port valve 111 being in a second position. The solid lines between ports within the ten port switching valve 111 indicate fluid connections between the ports.

In the second position, depicted in FIG. 2, the second sample is eluted from the second column 117 by the pumping of solvents from the gradient system 101 through the second column 117 with a fixed percent of acetonitrile at 50% volume/volume. The second sample is eluted from the second column 117 to the deposition module 120. In the second position the ten port valve 111 allows sample to be delivered to the first column 115 after it has been equilibrated in aqueous solvent. This first and second position within the ten port switching valve 111 allows parallel processing of sample. This parallel processing allows the first column to be prepared by flushing the column with appropriate solvents before receiving a sample while the second column is concentrating and desalting a previously received sample.

Figure 3:
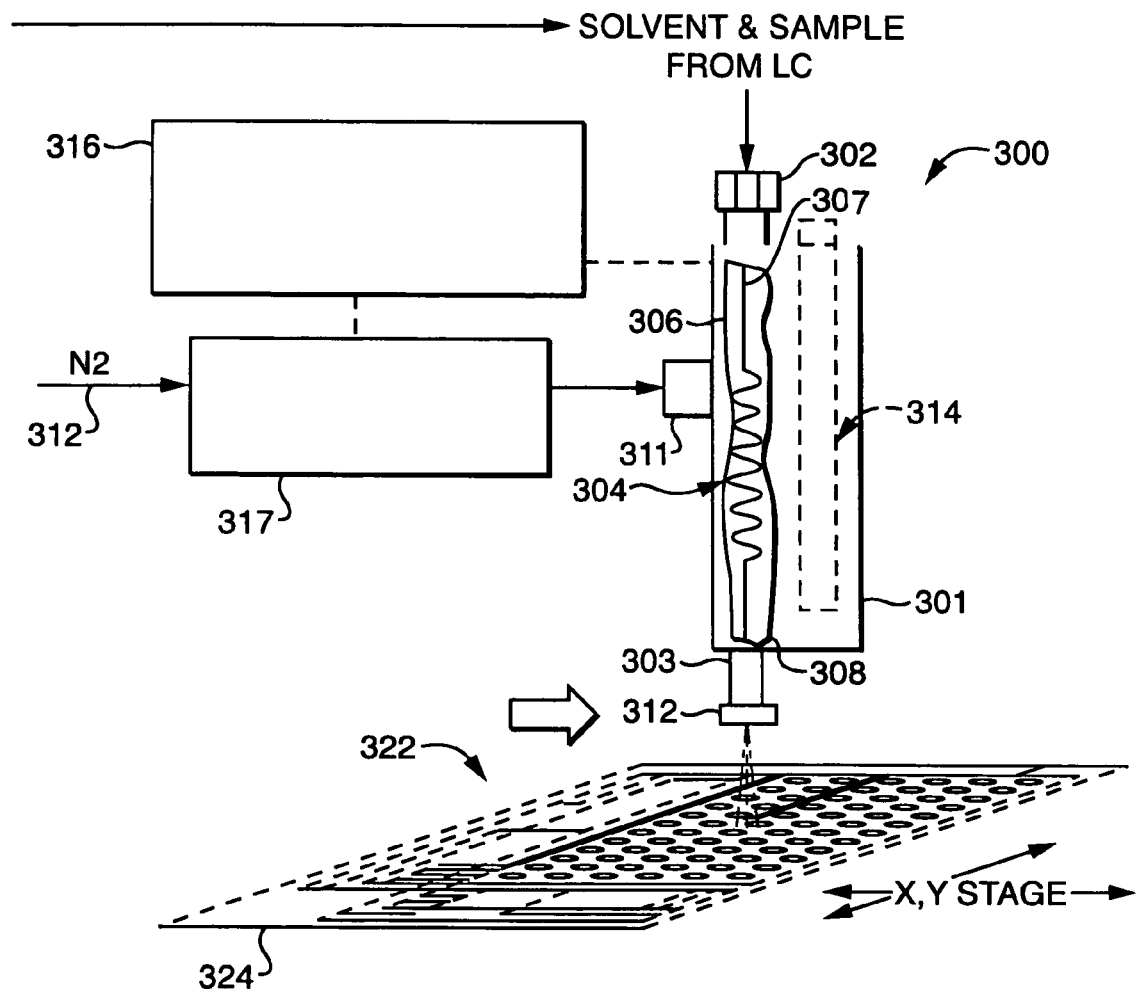
FIG. 3 depicts a nebulizer used in the inventive system to deposit sample onto a MALDI target.

Once the sample is received by the respective columns 115, 117, the sample is concentrated and desalted. The sample is then eluted and delivered to the deposition module 120. As shown in FIG. 3, the deposition module 120, within the inventive system, is a nebulizer 300. The nebulizer is formed from a metallic block 301. The metallic block 301 has an inlet port 302 and an outlet port 303. The inlet port 302 is connected to an approximately 30 cm long by 100 um internal diameter (i.d.) coiled capillary tube 304 that is coiled within a cavity 306 in the metallic block 301. This capillary tube can range from approximately 10 um i.d. to 500 um i.d. The length can range from approximately 5 cm to 60 cm. The tubing can be made of stainless steel or fused silica. It is contemplated within the scope of the invention that other alternative capillary tubing that is bio-compatible and inert to system solvents may be used. This alternative capillary tubing may be fabricated from materials such as titanium or the like.

The coiled capillary tubing 304 has a first end 307 and a second end 308. The first end 306 is connected to the inlet port 302. The second end 308 is connected to the outlet port 303. The outlet port 303 is connected to a spray nozzle 312. The metallic block 301 has a programmable block heater 314 that heats the metallic block 301 through an electrical resistance heating element. It is contemplated within the scope of the invention that other methods known in the art may be used to heat the metallic block 301 such as a peltier heat pump, or the like.

The nebulizer 300 has a temperature controller 316 that monitors the heat of the metallic block 301. The nebulizer 300 has a gas inlet port 311 within the metallic block 301. The gas inlet port 311 is connected to the cavity 306. The gas inlet port is connected to a sheath gas supply line 312 that is equipped with a sheath gas preheater 317. The nebulizer 300 of the present invention receives sample material that is eluted from the columns as discussed above. These sample materials are heated to a certain temperature from about 20° C. to 150° C., causing the sample material to vaporize. This vaporized material is enveloped in a sheath of non-reactive gas, such as nitrogen. It is contemplated within the scope of this invention that other non-reactive gases known in the art may be used such as Helium, Argon or the like. This non-reactive gas confines and entrains the vaporized sample material and aids in the evaporation of solvent remaining within the sample such that substantial solvent evaporation occurs before the vaporized sample is deposited on a MALDI target surface 322.

It is desirable within the present invention that trace amounts of solvent remain within the sample material to allow sample material to dissolve within the MALDI target surface 322 that can be coated with MALDI matrix. The nebulizer 300 of the instant invention utilizes the programmable heater 314 to vaporize and deposit sample in a continuous strip onto a MALDI target surface 322, which can be a MALDI matrix upon a conductive foil. The nebulizer 300 of the present invention is further described in a patent to Prevost et al. U.S. Pat. No. 5,772,964, the teachings of which are incorporated herein in their entirety by reference.

The vaporized sample material is deposited on a MALDI target surface 322, which in this first illustrative embodiment is Waters LC-MALDIprep™ Targets. It is contemplated within the scope of the invention that other MALDI targets and preparation methods known in the art may be used such as spin coated MALDI matrix, plain stainless steel , DIOS surfaces, dried droplet method, thin layer method, or the like.

The MALDI target 322 is edge registered in a programmable moving platen 324 by the use of a plate holder. This computer programmable moving platen 324 is controlled to track the efficient retrievable placement of sample material upon the MALDI target 322 for analysis. The sample material is sprayed upon the MALDI target 322 by the nebulizer 300 in continuous strips for subsequent retrievable analysis with a MALDI mass spectrometer.

In the illustrative embodiment, the data processor is a general purpose computer, such as an Intel Pentium® based personal computer running Microsoft Windows® XP or Windows NT. It is contemplated within the scope of the invention that other processors known in the art may be used.

Figure 4:
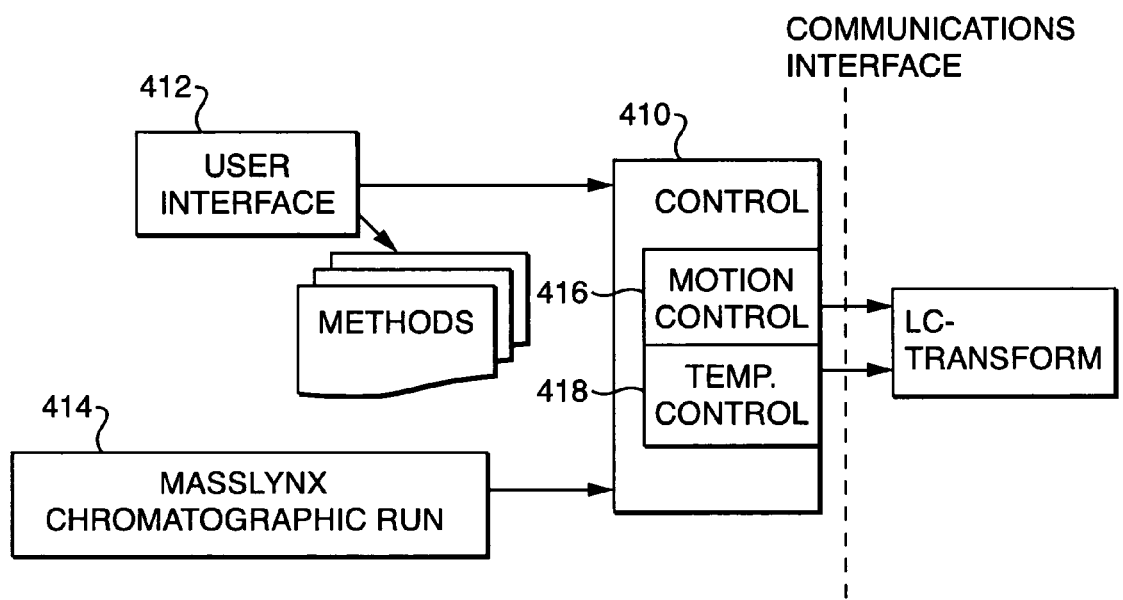
FIG. 4 depicts a schematic of the programmable control system of the invention.

The processing and control application software is either MassLynx® or the Stand alone LC-MALDI prep software as produced by Waters Corporation of Milford, Mass. MassLynx® comprises three major components as shown in FIG. 4. The main control 410 communicates with both a user interface 412 and a main MassLynx chromatographic control 414. The user interface 412 uses the main control 410 for diagnostic purposes such as ensuring accurate sample deposition. The main control 410 disseminates method data to control modules, which in the instant invention involve a motion control 416 and a temperature control 418. The motion and temperature controllers within the nebulizer and movable platen have distinct communication lines with the control modules. This control software allows a chromatographer to control instrumentation, and to acquire and deposit sample material onto a MALDI target. It also allows the chromatographer to process those MALDI target samples and to store, retrieve and display, location of sample material.

Another component is the application software that processes and extracts information from the data and presents it in reports. A report generator allows the user to create, manage and print reports. A graphical user interface (GUI) allows the user to interact with all these subsystems and components from the monitor. The illustrative embodiments of the present invention are implemented within the data processing component of MassLynx®.

EXAMPLE 1

Figure 5:
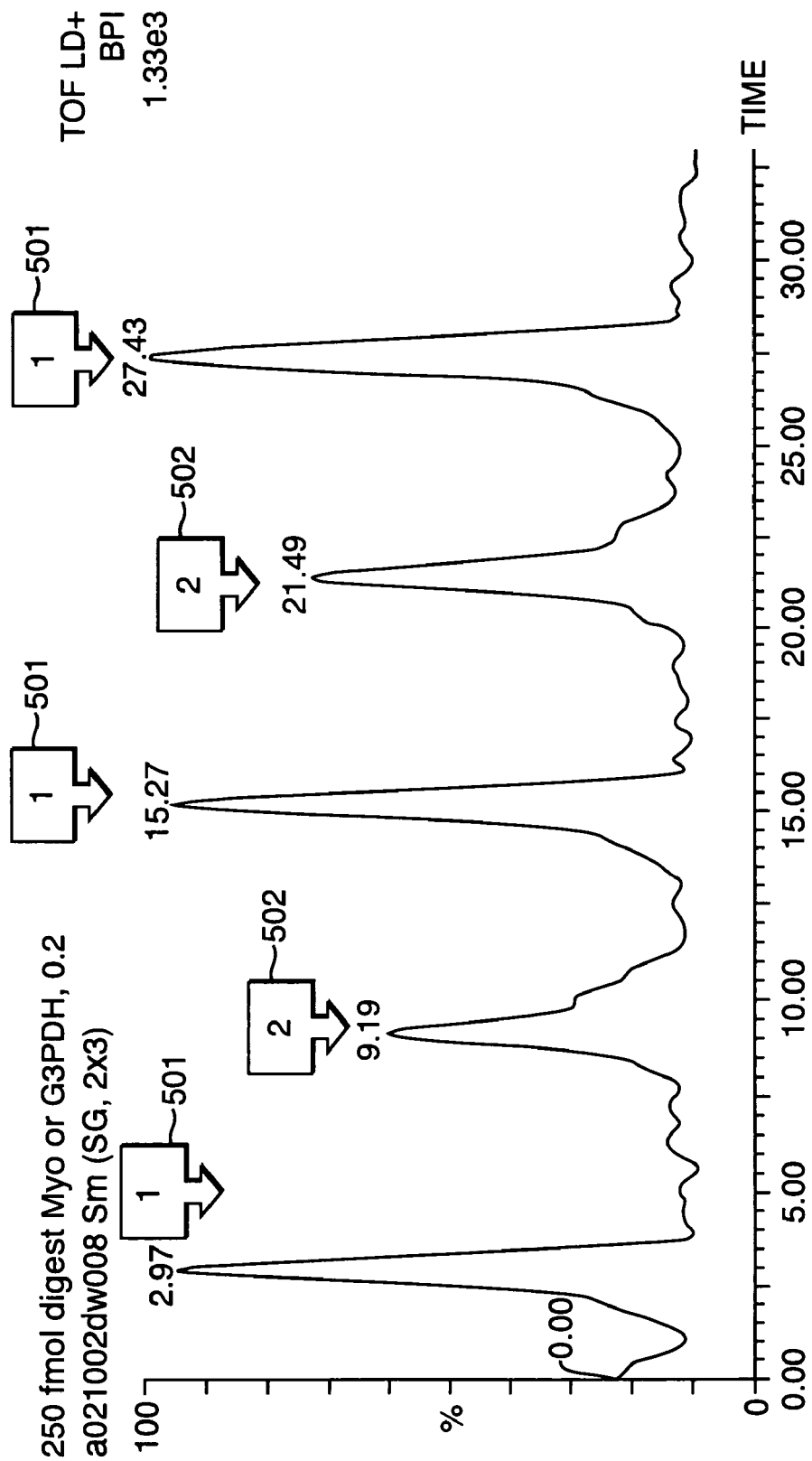
FIG. 5 depicts the reproducibility of the detector response from the first and second column.

The performance of the inventive method was tested using several protein digests that were deposited on a MALDI target. Two samples were used to demonstrate the reproducibility of MALDI spectra, especially with the off-line parallel processing method of this instant invention. The two samples used were tryptic digests of Myoglobin and Glyceraldehyde-3-PO4-dehydrogenase. The samples were parallel processed according to the inventive method and the eluent from a reversed phase HPLC peptide elution of the two samples were continuously deposited onto a MALDI sample plate (pre-coated with αCHCA matrix). The results of this are shown in FIG. 5 the sample containing Myoglobin 501 and the sample containing Glyceraldehyde-3-PO4-dehydrogenase 502 were parallel processed showing good reproducibility of MALDI mass spectral response.

Figure 6A:
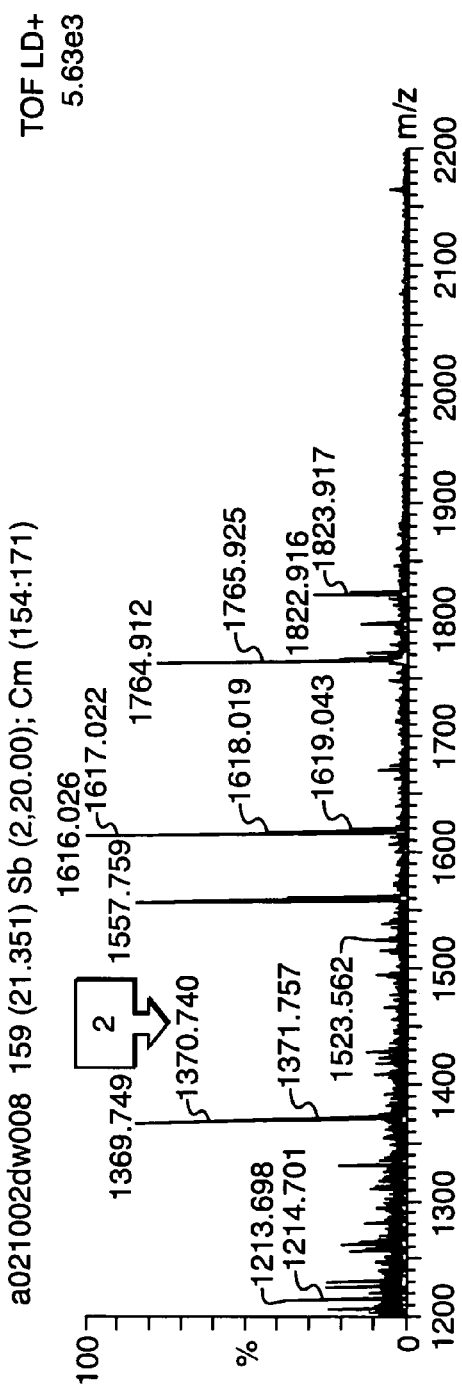
FIGS. 6A and 6B depict the mass spectrometer of samples from the first column and the second column.
Figure 6B:
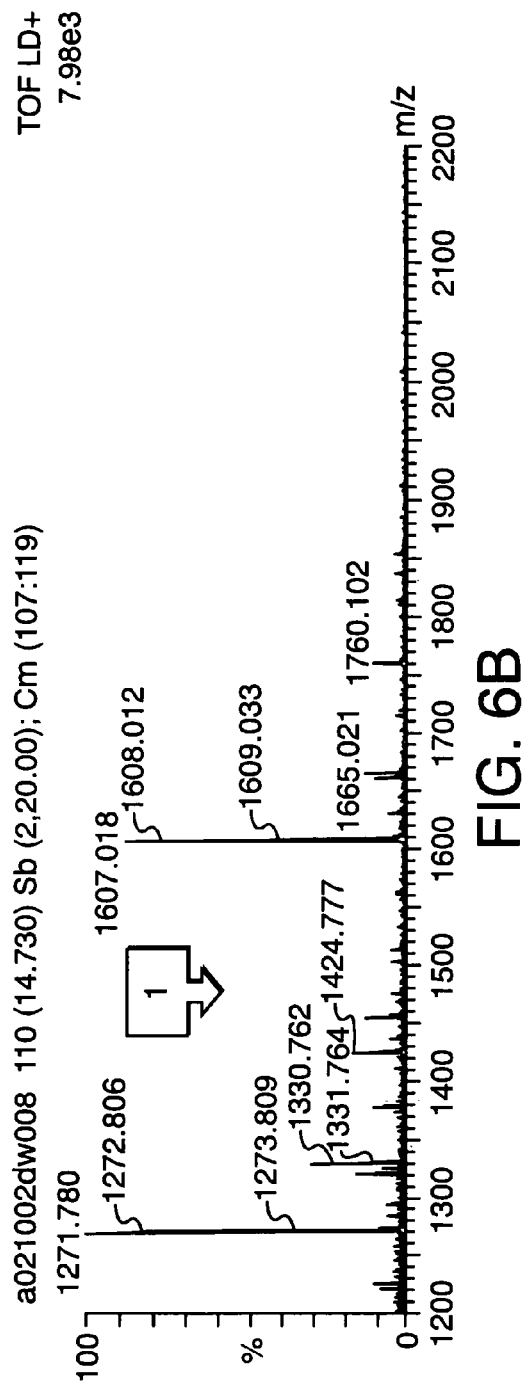

Turning to FIGS. 6A and 6B the mass spectrometer analysis of the two samples is depicted. The spectral analysis of the Myogoblin digest is shown in FIG. 6B and the spectral analysis of the G3PDH digest is shown in FIB 6A.

Although the illustrative embodiments of the instant invention utilizes two chromatography columns that are operated in parallel, it should be appreciated by those skilled in art that with additional ports in the switching valve that additional multiples of chromatography columns may be used. Likewise with the use of additional chromatography columns, it should be appreciated that additional multiples of solvent delivery systems and auto samplers may be used in conjunction with additional multiples of chromatography columns to achieve parallel processing having an even greater throughput than the illustrative embodiment.

Although the illustrative embodiments of the instant invention utilize pre-coated MALDI matrix targets, it should be appreciated by those skilled in the art that other target substrates known in the art may be used.

Although the illustrative embodiments of the instant invention utilize MALDI ionization methods, it should be appreciated by those skilled in the art that other detection methods known in the art may be used such as MALDI Ion Trap, MALDI Q-TOF, MALDI TOF TOF or the like.

Although the illustrative embodiments of the instant invention utilize MADLI targets and detection methods, it should be appreciated that other targets and detection methods such as Desorption Ionization On Silicone (DIOS) may be used.

Although the illustrative embodiments of the instant invention utilizes two chromatography columns in parallel, it should be appreciated by those skilled in the art that in order to increase throughput of the parallel columns one can use multiple column arranged in serial within each parallel configuration to further increase throughput.

Although the illustrative embodiments deposit a sample upon a MALDI matrix, it should be appreciated by those skilled in the art that a MALDI matrix material can be mixed with an analyte downstream from the columns and prior to neubiliztion where said neublized sample contains MALDI matrix material.

Although elements of the illustrative embodiment are described as in fluid communication with each other, it should be appreciated by those skilled in the art that such communication can result from direct or indirect connections between such elements.

Although the invention has been shown and described with respect to exemplary embodiments thereof, various other changes, omissions and additions in the form and detail thereof may be made therein without departing form the spirit and scope of the invention.

What is claimed is:

1. A method for the parallel processing of samples comprising the steps of:
   providing a first chromatography column and a second chromatography column said first and second chromatography columns being in fluid communication with a multi port switching valve;
   providing a solvent delivery system in fluid communication to said multi port switching valve;
   providing a sample injector in fluid communication to said multi port switching valve;
   providing a nebulizer being in fluid communication to said multi port switching valve, said nebulizer comprising a capillary tube having a length greater than about 5 cm;
   injecting a first sample into said first chromatography column;
   concentrating said first sample;
   delivering said first sample to said capillary tube of said nebulizer;
   nebulizing said first sample, wherein nebulizing said first sample comprises heating said capillary tube;
   depositing said first sample on a MALDI target;
   flushing said first column preparing for additional samples;
   injecting a second sample into said second chromatography column while said first chromatography column is being prepared for additional samples;
   concentrating said second sample;
   delivering said second sample to said capillary tube of said nebulizer;
   nebulizing said second sample, wherein nebulizing said second sample comprises heating said capillary tube; and
   depositing said second sample on said MALDI target.

2. The method according to claim 1 wherein said capillary tube comprises a coiled capillary tube.

3. The method according to claim 1 wherein said first and second chromatography columns are reverse phase HPLC columns.

4. The method according to claim 1 wherein said samples are spray deposited on said MALDI target by nebulizing said samples by application of heat and enveloping said sample in a sheath of non-reactive gas which confines and entrains said spray and aids in the evaporation of solvent within said sample.

5. The method according to claim 1 wherein said concentration of said sample within said first chromatography column occurs while said second column is prepared to receive said second sample by flushing said second column with solvent and said multi port switching valve continuously alternates concentration and preparation between said columns.

6. The method according to claim 1 wherein said depositing of said sample is automated by a programmable control system and said sample is deposited on said MALDI target in a retrievable pattern.

7. The method according to claim 1 wherein said sample deposited on said MALDI target contains trace amounts of solvents allowing said sample to penetrate said MALDI target.

8. The method according to claim 4 wherein said non-reactive gas is heated prior to enveloping said sample.

9. The method according to claim 1 wherein said MALDI target is positioned upon a programmable movable platen allowing for a retrievable pattern of samples.

10. The method according to claim 1 wherein said solvent delivery system is comprised of two solvent reservoirs that are delivered by single syringe pumps.

11. The method according to claim 1 wherein a MALDI matrix material is mixed with the sample prior to nebulizing said sample.

12. An apparatus for the parallel processing of samples comprising:
  a first chromatography column and a second chromatography column;
  a multi port switching valve being in fluid communication to said first and second chromatography columns;
  a solvent delivery system in fluid communication with said multi port switching valve;
  a sample injector in fluid communication with said multi port switching valve;
  a nebulizer being in fluid communication with said multi port switching valve, said nebulizer comprising a heated capillary tube having a length greater than about 5 cm, said nebulizer depositing samples received from said first and second chromatography columns onto a movable MALDI target by nebulizing said samples; and
  a programmable control module controlling said solvent delivery system, said sample injector, said multi port switching valve and said nebulizer, whereby multiple samples are parallel processed by said first and second chromatography columns and deposited onto MALDI targets in a retrievable pattern.

13. The apparatus according to claim 12 wherein said capillary tube comprises a coiled capillary tube.

14. The apparatus according to claim 12 wherein said first and second chromatography columns are reverse phase HPLC columns.

15. The apparatus according to claim 12 wherein said nebulizer spray deposits samples on said MALDI target by vaporizing said samples by application of heat and enveloping said sample in a sheath of non-reactive gas which confines and entrains said spray and aids in the evaporation of solvent within said sample.

16. The apparatus according to claim 12 wherein said first chromatography column and said second chromatography column are switched between concentration and separation by said multi port switching valve where said multi port switching valve continuously alternates between separation and preparation states between said columns.

17. The method according to claim 15 wherein said non-reactive gas is heated prior to enveloping said sample.

18. The apparatus according to claim 12 wherein said movable MALDI target is positioned upon a programmable movable platen.

19. The apparatus according to claim 12 wherein said solvent delivery system is comprised of two solvent reservoirs that are delivered by single syringe pumps.

20. The method of claim 1, wherein depositing said first and second samples on the MALDI target comprises forming a continuous strip on the MALDI target.

21. The method of claim 1, wherein the length of the capillary tube of the nebulizer is greater than about 20 cm.

22. The method of claim 1, wherein the nebulizer further comprises a heated metallic block defining a cavity within which the capillary tube is disposed.

* * * * *